(12) United States Patent
Suresh et al.

(10) Patent No.: US 10,908,092 B2
(45) Date of Patent: Feb. 2, 2021

(54) PROCESS FOR MAKING CYANO FUNCTIONALIZED GOLD NANOPARTICLES

(71) Applicants: Radhika Suresh, Sugar Land, TX (US); Sankaran Murugesan, Katy, TX (US); Valery N. Khabashesku, Houston, TX (US); Qusai Darugar, Houston, TX (US)

(72) Inventors: Radhika Suresh, Sugar Land, TX (US); Sankaran Murugesan, Katy, TX (US); Valery N. Khabashesku, Houston, TX (US); Qusai Darugar, Houston, TX (US)

(73) Assignee: BAKER HUGHES, A GE COMPANY, LLC, Houston, TX (US)

( * ) Notice: Subject to any disclaimer, the term of this patent is extended or adjusted under 35 U.S.C. 154(b) by 196 days.

(21) Appl. No.: 16/157,574

(22) Filed: Oct. 11, 2018

(65) Prior Publication Data

US 2020/0116640 A1    Apr. 16, 2020

(51) Int. Cl.
*G01N 21/63* (2006.01)
*G01N 21/78* (2006.01)
*G01N 21/65* (2006.01)

(52) U.S. Cl.
CPC ........... *G01N 21/658* (2013.01); *G01N 21/78* (2013.01)

(58) Field of Classification Search
CPC ...... G01N 21/658; G01N 21/65; G01N 21/63; G01N 21/62; G01N 21/78; G01N 21/77; G01N 21/75
USPC .......................................................... 436/8
See application file for complete search history.

(56) References Cited

U.S. PATENT DOCUMENTS

| 7,017,271 | B1 | 3/2006 | Parsons et al. |
| 8,980,179 | B2* | 3/2015 | Geddes ................ G01N 33/553 |
| | | | 422/82.02 |
| 10,025,000 | B2 | 7/2018 | Monteiro et al. |
| 2006/0050268 | A1 | 3/2006 | Talley et al. |
| 2008/0149479 | A1* | 6/2008 | Olofsson ................ B82Y 30/00 |
| | | | 204/403.14 |

(Continued)

FOREIGN PATENT DOCUMENTS

WO    2012083027 A1    6/2012

OTHER PUBLICATIONS

International Search Report and Written Opinion for International Application PCT/US2019/055005; International Filing Date: Oct. 10, 2019; dated Jan. 17, 2020; 11 pages.

(Continued)

*Primary Examiner* — Christine T Mui
(74) *Attorney, Agent, or Firm* — Cantor Colburn LLP

(57) ABSTRACT

A cyanide-functionalized gold nanoparticle. A method of making cyanide-functionalized gold nanoparticles includes forming an aqueous reaction mixture comprising a gold precursor and glycine, keeping the reaction mixture at about 18° C. to about 50° C. for at least 6 days to provide formation of the cyanide-functionalized gold nanoparticles, and isolating the cyanide-functionalized gold nanoparticles from the reaction mixture. A method of analyzing a sample, comprising contacting cyanide-functionalized gold nanoparticles with the sample and performing an analytical method on the sample. A sensor comprises cyanide-functionalized gold nanoparticles.

8 Claims, 5 Drawing Sheets

(56) References Cited

U.S. PATENT DOCUMENTS

| | | |
|---|---|---|
| 2012/0156709 A1 | 6/2012 | Bertin et al. |
| 2014/0373649 A1 | 12/2014 | Harrell et al. |
| 2017/0285211 A1 | 10/2017 | Monteiro et al. |
| 2018/0067054 A1 | 3/2018 | Suresh et al. |

OTHER PUBLICATIONS

Agasti et al. "Synthesis of water soluble glycine capped silver nanoparticles and their surface selective interaction" Materials Research Bulletin, vol. 64; 2015; pp. 17-21.

Cai, et al.; "Gold Nanoparticles with Different Amino Acid Surfaces: Serum Albumin Adsorption, Intracellular Uptake and Cytotoxicity"; Colloids and Surfaces B: Biointerfaces; vol. 123; 2014; pp. 900-906.

Cheng, et al; "Synthesis of Gold Nanoparticles"; Department of Chemistry; State University of New York at Binghamton; Binghamton, NY, USA; 2014; pp. 37-79.

Crespilho, et al., "The Origin of the Molecular Interaction Between Amino Acids and Gold Nanoparticles: A Theoretical and Experimental Investigation"; Chemical Physics Letters, vol. 469; 2009; pp. 186-190.

Csapo et al.; "Influence of pH and aurate/amino acid ratios on the tuneable optical features of gold nanoparticles and nanoclusters"; Colloids and Surfaces A: Physicochemical and Engineering Aspects, vol. 532; 2017; pp. 601-608.

Doyen et al.; "Amino Acid Induced Fractal Aggregation of Gold Nanoparticles: Why and How"; Journal of Colloid and Interface Science, vol. 464; pp. 160-166; (2016).

Hamaguchi, et al.; "Photochemical Synthesis of Glycinestabilized Gold Nanoparticles and its Heavy-Metal-Induced Aggregation Behavior"; Colloids and Surfaces A: Physicochem. Eng. Aspects, vol. 367; 2010; pp. 167-173.

Lee et al., "Selective and Rapid Room Temperature Detection of H2S Using Gold Nanoparticle Chain Arrays,"; Electroanalysis, Short Communication, vol. 23, Issue No. 11; 2011; pp. 2623-2628.

Majzik, et al.; "Functionalization of Gold Nanoparticles with Amino Acid, B-amyloid Peptides and Fragment"; Colloids and Surfaces B: Biointerfaces, vol. 81; 2010; pp. 235-241.

Maruyama, et al.; "Synthesis of Gold Nanoparticles Using Various Amino Acids"; Journal of Colloid and Interface Science, vol. 447; 2015; pp. 254-257.

Sharma, et al.; "Biologically Active L-Cysteine as a Reducing/ Capping Agent for Controlled Tuning of Gold Nanoparticles"; Journal of Alloys and Compounds, vol. 649; 2015; pp. 11-18.

Wangoo, et al., "One Pot, Rapid and Efficient Synthesis of Water Dispersible Gold Nanoparticles Using Alpha-Amino Acids"; Nanotechnology, vol. 25, Issue No. 43; 2014; 7 pages.

Zhou et al.; "State of the Art in Gold Nanoparticle Synthesis"; Coordination Chemistry Reviews, vol. 257; 2013; pp. 638-665.

Zhou, et al., "Functionalized Gold Nanoparticles: Synthesis, Structure and Colloid Stability"; Journal of Colloid and Interface Science, vol. 331; 2009; pp. 251-262.

* cited by examiner

PROCESS FOR MAKING CYANO FUNCTIONALIZED GOLD NANOPARTICLES

BACKGROUND

SERS (Surface Enhanced Raman Spectroscopy) is an analytical technical that allows detection of low concentration chemicals. Some of the key parameters to consider when developing a SERS detection method include specificity, linearity, accuracy, precision, range, limit of detection (LOD) and limit of quantification (LOQ). Instrumental factors to be considered include laser power, optical alignment, resolution of spectrometer, and sensitivity of the detector. In order to overcome these limitations, internal standards are often used to provide stable calibration and quantitative measurements.

What are needed are plasmonic nanoparticles with suitable functional groups, which act as internal standards for SERS methods and convenient and reliable methods for making the internal standards. The nanoparticles can be used in additional analytical methods.

SUMMARY

Included herein is a cyanide-functionalized gold nanoparticle.

A method of making cyanide-functionalized gold nanoparticles includes forming an aqueous reaction mixture comprising a gold precursor and glycine, keeping the reaction mixture at about 18° C. to about 50° C. for at least 6 days to provide formation of the cyanide-functionalized gold nanoparticles, and isolating the cyanide-functionalized gold nanoparticles from the reaction mixture.

A method of analyzing a sample includes contacting cyanide-functionalized gold nanoparticles with the sample and performing an analytical method on the sample.

A sensor includes a cyanide-functionalized gold nanoparticle.

BRIEF DESCRIPTION OF THE DRAWINGS

The following descriptions should not be considered limiting in any way. With reference to the accompanying drawings, like elements are numbered alike.

DETAILED DESCRIPTION

Figure 1:
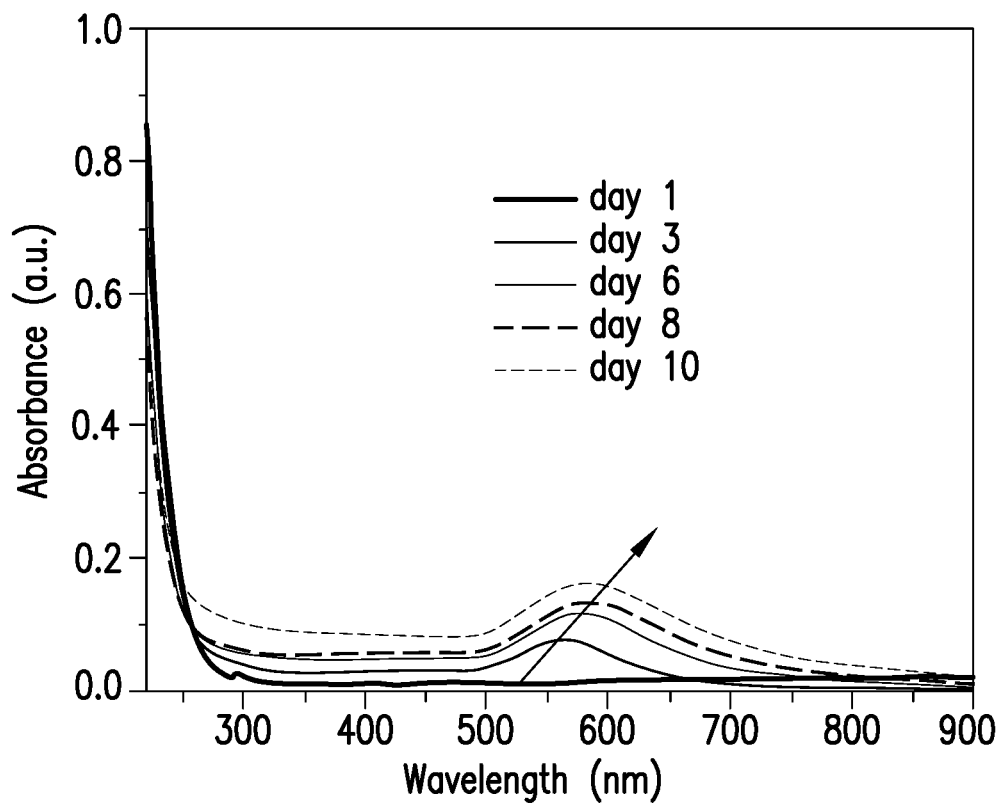
FIG. 1 shows the UV-visible analysis of the reaction mixture to form cyanide-functionalized gold nanoparticles (AuNPs) as a function of time in days. A plasmonic band is observed after day 6.

A detailed description of one or more embodiments of the disclosed compositions and methods are presented herein by way of exemplification and not limitation with reference to the Figures.

Provided herein are Au nanoparticles (AuNPS) having a unique functional group (cyanide) attached to the Au surface, as well as methods of making the particles and methods of using the particles. The cyanide peak of the cyanide-functionalized AuNPs at around 2100 cm$^{-1}$ can provide an internal standard and reference peak for calibration and quantitative analysis in SERS applications because the cyanide attached to the AuNPs remains constant throughout the analytical measurements. The cyanide-functionalized AuNPs have utility in analytical methods other than SERS and also in sensors.

In the method of making the cyanide-functionalized AuNPs, the cyanide functionalization is formed using the amino acid glycine as a reactant. While amino acid based synthesis of AuNPs nanoparticles has been used previously, important features of the process described herein include a thermodynamically driven process (e.g., reaction at room temperature), a unique way to form an AuNP complex, and formation of a selective cyanide bond over the AuNP surface. Glycine is particularly suited for cyanide bond formation as it acts as both a reducing and capping agent in the synthesis. Another unique feature of the synthesis method described herein is the transformation of glycine into cyano functionality involving —COOH and —NH$_2$. The transformation of glycine into cyanogen chloride/cyanide while reducing a gold salt has not been previously described.

In an aspect, described herein is a cyanide-functionalized gold nanoparticle. In an embodiment, the cyanide-functionalized gold nanoparticles have an average diameter of about 10 nm to about 200 nm. In an aspect, the cyanide covers about 0.1% to about 40% of the nanoparticle surface.

In an aspect, a method of making cyanide-functionalized gold nanoparticles comprises forming an aqueous reaction mixture comprising a gold precursor and glycine, keeping the reaction mixture at a temperature of about 18° C. to about 50° for at least 6 days to provide formation of the cyanide-functionalized gold nanoparticles, and isolating the cyanide-functionalized gold nanoparticles from the reaction mixture. In an embodiment, the reaction is performed in the dark, preferably without stirring. Isolating the cyanide-functionalized gold nanoparticles from the reaction mixture can include filtering or centrifuging, for example.

Exemplary gold precursors include chloroauric acid, gold (III) chloride; gold (III) iodide, trichloro(pyridine)gold(III), chloro(triphenylphosphine)gold(I), gold(I) cyanide, gold (III) bromide, gold(I) sulfide, gold(III) hydroxide, chloro (triethylphosphine)gold(I), methyl(triphenylphosphine)gold (I), or a salt thereof. Example gold precursors include a sodium salt or a potassium salt such as potassium gold (III+) chloride. In an embodiment, the gold precursor comprises [AuCl$_4$]$^-$. A preferred gold precursor is K[AuCl$_4$].

In an embodiment, the reaction mixture comprises 0.001 to 1 wt %, specifically 0.01 to 0.1 wt % of the gold salt, and 0.001 to 1 wt %, specifically 0.01 to 0.1 wt % of the glycine, based on the weight of the reaction mixture.

In another embodiment, the reaction mixture has a pH of about 7 to about 14, specifically, about 9 to about 11. In an embodiment, the reaction is performed without stirring.

In an embodiment, the method further comprises monitoring the formation of the cyanide-functionalized gold nanoparticles by UV-visible spectroscopy, dynamic light scattering particle analysis, Raman spectroscopy, or a combination comprising at least one of the foregoing. Monitoring the formation of the cyanide-functionalized gold nanoparticles by UV-visible spectroscopy can comprise monitoring absorbance at 500-700 nm. Dynamic light scattering particle analysis can comprise determining the mean particle diameter of the nanoparticles. Raman spectroscopy can comprise monitoring the cyanide peak around 2100 $cm^{-1}$.

An advantage of the cyanide-functionalized gold nanoparticles is that the cyanide bond act as a reference and marker in analytical techniques such as SERS.

In an embodiment, a method of analyzing a sample comprises contacting cyanide-functionalized gold nanoparticles with the sample and performing an analytical method on the sample.

In an embodiment, the analytical method comprises radiating the sample contacted with the cyanide-functionalized gold nanoparticles with electromagnetic radiation; measuring a Raman spectrum emitted from the sample; and determining the presence or a concentration of a selected chemical in the sample from the Raman spectrum, wherein the cyanide-functionalized gold nanoparticles provide an internal reference at about 2,100 $cm^{-1}$. In an embodiment, the Raman spectroscopy is SERS.

SERS is a surface-sensitive detection technique that is used to detect molecules adsorbed on rough metal surfaces or nanostructures. The methods disclosed herein can employ cyanide-functionalized gold nanoparticles as a SERS substrate. The unique substrate provides enhancements in Raman signals of the adsorbed molecules in an order of up to $10^6$. The enhancement allows the detection and/or measurement of chemicals such as amines at parts per million (ppm) or even parts per billion (ppb) levels. Moreover, the cyanide-functionalized gold nanoparticles have a unique and strong peak which can be used as an internal standard for calibration purpose so that the results are consistent from batch to batch.

The cyanide-functionalized gold nanoparticles can be in the form of a sol or colloidal suspension of functionalized metallic nanoparticles in a fluid such an aqueous fluid. In another aspect, cyanide-functionalized gold nanoparticles can be in the form of substrate for SERS comprising a first layer of cyanide-functionalized gold nanoparticles and a second layer of a support layer. The support layer comprises glass, silica, ceramics, a polymer such as polydimethylsiloxane, graphene, carbon nanotubes, silicon wafers, ceramics, ceramics, or a combination comprising at least one of the foregoing. The functionalized metallic nanoparticles can be deposited or coated on the support layer. In yet another aspect, cyanide-functionalized gold nanoparticles can be in the form of a matrix such as glass, silica, or a polymer such as polydimethylsiloxane comprising the cyanide-functionalized gold nanoparticles.

Raman spectroscopy can be used to detect the presence or concentration of a selected chemical in the sample. In an embodiment, the sample can include a fluid such as refinery fluid, a production fluid, cooling water, process water, drilling fluids, completion fluids, production fluids, crude oil, feed streams to desalting units, outflow from desalting units, refinery heat transfer fluids, gas scrubber fluids, refinery unit feed streams, refinery intermediate streams, finished product streams, and combinations thereof. As a specific example, the fluid is a hydrocarbon extracted from a reservoir in an earth formation or a further processed fluid thereof. A further processed fluid refers to a fluid that has been treated to remove undesired materials or solid, if any. As another specific example, the sample is an aqueous based fluid such as sour water or treated sour water. The sample can be directly analyzed. However, if desired, the sample can be pre-purified before being analyzed to remove undesired impurities in solid or liquid forms. Such pre-purification includes filtration, column treatment, and other methods known to a person skilled in the art.

The methods are effective to determine selected chemicals at a concentration of equal to or greater than about 1 parts per billion (ppb) to about 1,000 parts per million (ppm) or at a concentration of equal to or greater than about 1 ppm to about 1,000 ppm.

Any Raman spectrometer known in the art can be used. In use, electromagnetic energy is directed at the sample from an energy source of the Raman spectrometer. The energy source can be a laser; and the electromagnetic energy can be a monochromatic beam provided at a frequency or energy level that is attuned to at least one of a vibrational or rotational excitation of the chemical of interest in the sample. The electromagnetic energy excites the electrons of the chemical of interest to a virtual energy state. As the excited electrons fall back into a lower energy state, it emits photons that can be either lower energy (Stokes scattering) or higher energy (anti-Stokes scattering) than the energy of the incident electromagnetic energy. The emitted photons are received at a detector of the spectrometer. The detector generates signals indicative of the energy of the received photon. The signals are then sent to a control unit for processing.

The control unit includes a processor, a memory storage device, generally a solid-state memory storage device, and one or more programs stored in the memory storage device and accessible to the processor. When the one or more programs are executed or run by the processor, the processor produces a spectrum of the emitted photons. The spectrum can be observed or reviewed in order to identify chemicals and relative chemical concentrations within the sample. The processor can determine the presence or absence of a selected chemical in the sample or determine the concentration of a chemical in the sample. The processor can also provide control signals to various components to control a level of the chemicals. The control unit can be part of the Raman spectrometer or can be independent of the Raman spectrometer.

Included herein are sensors comprising the cyanide-functionalized AuNPs described herein.

Figure 8:
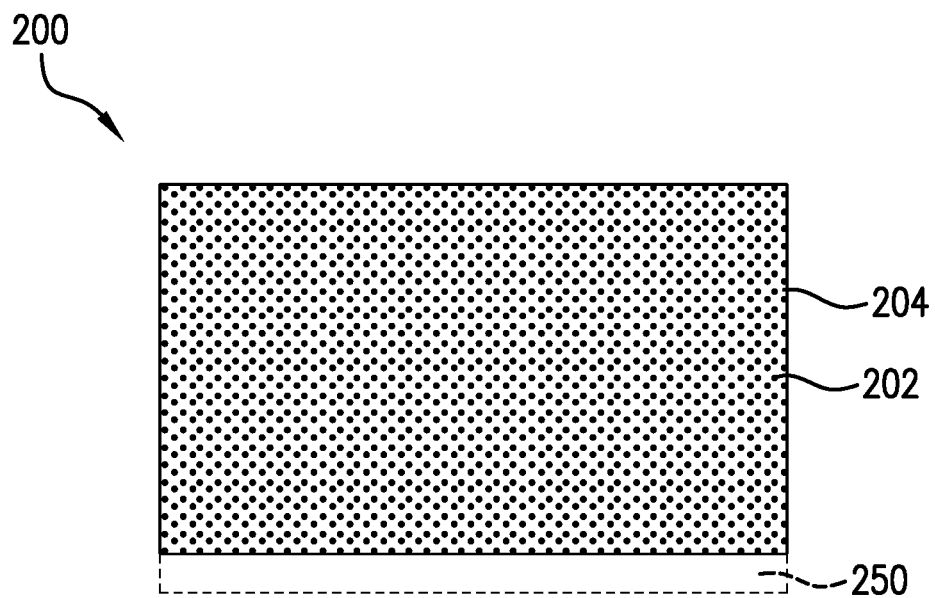
FIG. 8 shows a simplified cross-sectional view of a sensor comprising an optically sensitive material comprising the cyanide-functionalized AuNPs described herein.

In an embodiment, included herein is an optically sensitive material 202 comprising the cyanide-functionalized AuNPs described herein. FIG. 8 shows an embodiment of a sensor 200 comprising an optically sensitive material 202 and a reflective material 250. The optically sensitive material 202 may be configured and formulated to react with an analyte of interest and form a reaction product that exhibits one or more unique optical properties. For example, one or more components of a wellbore fluid may chemically adsorb or physically adsorb onto the optically sensitive materials.

The optically sensitive material comprising the cyanide-functionalized AuNPs may be dispersed in a matrix material 204. Exemplary matrix materials include silica glass, borosilicate glass, quartz glass, or other optically transparent materials, such as polymers including polyvinylidene chloride, polyethers, polyacrylates, polysilicones, and the like, and combinations comprising at least one of the foregoing. A plurality of optically sensitive material 202 may be dispersed within the matrix material 204. The matrix material 204 may be doped with or impregnated with one or more of the optically sensitive materials 202. In some embodiments, the sensor 200 comprises a matrix material 204 having a substantially uniform concentration of the optically sensitive materials 202 dispersed therein.

Also included herein is a sensor comprising the cyanide-functionalized AuNPs described herein. FIG. 8 shows an embodiment of a sensor 200 with the optically sensitive material dispersed throughout the sensor 200. In some such embodiments, the sensor 200 may exhibit one or more unique optical properties responsive to chemical or physical adsorption of at least a component of the fluid to the sensor 200.

The sensor 200 is particularly useful to detect analytes in a fluid, e.g., a downhole fluid such as by operably coupling a radiation source to at least one optical fiber coupled to the sensor comprising the optically sensitive materials; contacting the sensor with the fluid suspected of containing an analyte; transmitting electromagnetic radiation from the radiation source through the at least one optical fiber to the sensor; and measuring at least one of an absorbance spectrum, an emission spectrum, a maximum absorption intensity, or a maximum emission intensity of electromagnetic radiation passing through the sensor after contacting at least some of the optically sensitive materials with the fluid. U.S. patent Ser. No. 10/025,000 is incorporated by reference herein for its disclosure of sensor and methods of detecting analytes.

Figure 9:
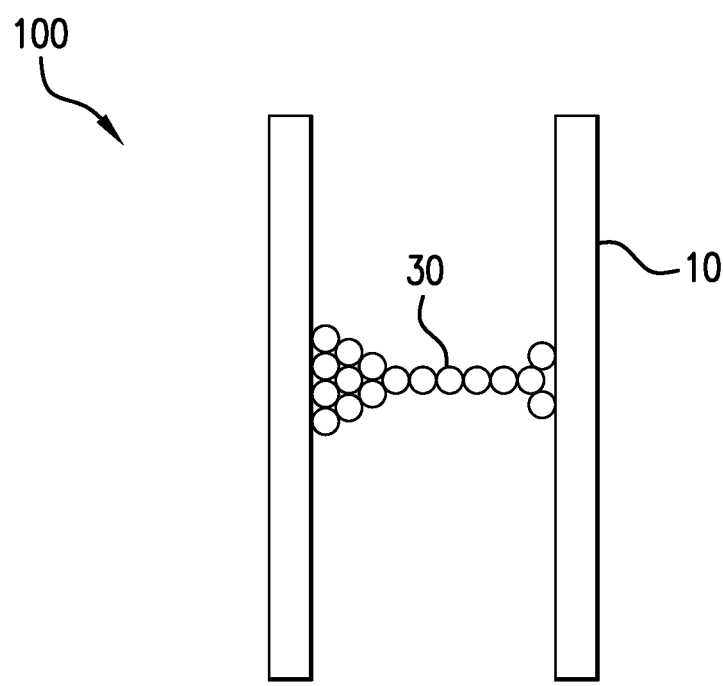
FIG. 9 shows a schematic illustration of a sensor for measuring hydrogen sulfide.

In another aspect, the cyanide-functionalized AuNPs can be used in sensors and methods of measuring hydrogen sulfide in fluids, e.g., downhole fluids. Nonlimiting examples of downhole fluids include a borehole fluid such as drilling, completion, workover and production fluids. In an aspect, FIG. 9 illustrates an embodiment of a sensor 100 comprising electrodes 10 and cyanide-functionalized AuNPs 30 bridging a gap between the electrodes 10.

In an embodiment, a method of determining the hydrogen sulfide concentration in a fluid comprises exposing a sensor to a fluid, e.g., a fluid within a wellbore; measuring a value of an electrical parameter of the sensor at an applied frequency of greater than about 10 kHz and a voltage of less than about 1.0 volt when the sensor is exposed to the fluid; and determining the concentration of hydrogen sulfide in the fluid based at least in part on the measured value of the electrical parameter. In an embodiment, determining the concentration of hydrogen sulfide in the fluid comprises comparing the measured value of the electrical parameter to a previously determined calibration curve or set of values of the electrical parameter of the sensor and correlating the measured value to the previously determined calibration curve or set of values. Exemplary electrical parameters include electrical resistance. Sensors 100 and methods of use thereof are described in U.S. Publication No. 20170285211, incorporated herein by reference for its disclosure of sensors and methods of determining hydrogen sulfide concentrations.

In yet another embodiment, the cyanide-functionalized AuNPs can be used to detect biological analytes in biological samples, such as detecting proteins, nucleic acids and cells. Exemplary biological methods include diagnostic methods, biomedical imaging, immunoassays, chromatography, therapeutic methods such as drug carriers and photodynamic therapy, and the like.

The invention is further illustrated by the following examples

Example 1: Synthesis of Cyanide-Functionalized AuNPs

Functionalized AuNPs were formed by providing an aqueous initial reaction mixture containing an Au salt and glycine in a clear solution. The reaction mixture included Salt K[AuCl$_4$] at a concentration of 0.016 wt %, and glycine at the same amount, at a pH of 9.5. The reaction mixture was kept in dark at room temperature and the growth process was monitored at certain time intervals through UV-Vis, dynamic light scattering (DLS) particle size analysis and Raman spectroscopy.

The initial reaction mixture did not show any plasmonic peaks in the UV-visible spectrum. As shown in FIG. 1, from the UV-visible analysis, an increase in a plasmonic band around 500-700 nm with respect to number of days was observed. The arrow indicates increased number of days. By day 6, a significant plasmonic band is observed.

DLS particle size analysis showed that particle size is around 70 nm on day 3 and grows to a maximum size of 90-100 nm and stays substantially the same after that. Raman analysis showed that there is no peak for initial reaction mixture.

Figure 2:
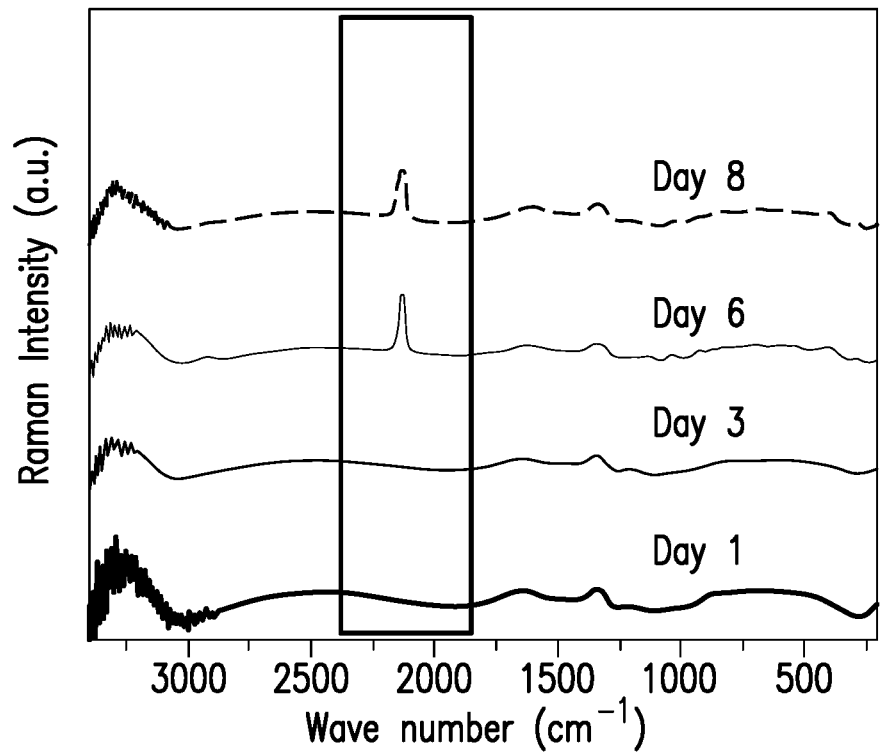
FIG. 2 shows the Raman analysis of the reaction mixture liquid as a function of time in days.

By day 3, the reaction mixture changed color from a colorless liquid to a reddish blue color. This liquid was used for Raman measurements. As shown in FIG. 2, the cyanide peak of the cyanide-functionalized AuNPs at around 2100 cm$^{-1}$ was visible at day 6. The day 6 sample showed a strong signature for the functionalized gold nanoparticles by Raman analysis.

Example 2: Further Characterization of Cyanide-Functionalized AuNPs

Figure 3:
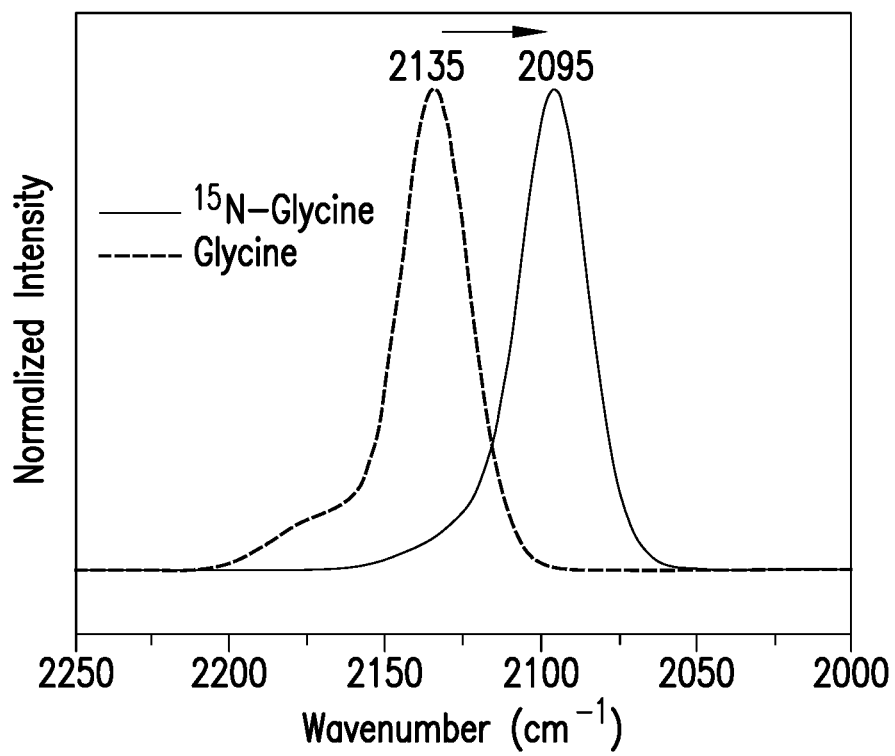
FIG. 3 shows the —CN peak shift by Raman spectroscopy indicating transformation of —NH$_2$ group of the glycine molecule into a —CN group.

Gold nanoparticles were synthesized and functionalized in-situ using glycine and glycine with $^{15}$N isotope according to the method of Example 1. The transformation of —NH$_2$ group of the glycine molecule into a —CN group is evident from the signal peak shift in Raman spectroscopy as shown in FIG. 3; the —CN peak at 2135 cm$^{-1}$ shifted to 2095 cm$^{-1}$ when $^{15}$N(—C$^{15}$N) was introduced.

Figure 4:
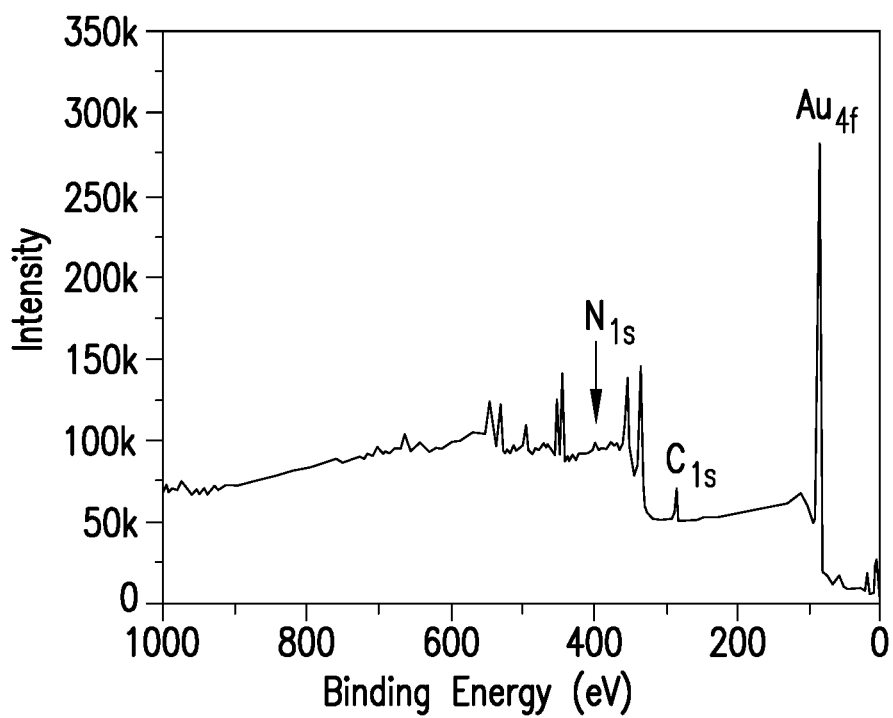
FIG. 4 shows an XPS survey spectrum of cyanide-functionalized AuNPs dried over Indium foil.

An XPS survey spectrum of cyanide-functionalized AuNPs dried over Indium foil was performed. The survey spectrum of FIG. 4 shows the presence of Au, C and N peaks as labeled. These peaks were then analyzed in high resolution to provide quantification and oxidization state.

Figure 5:
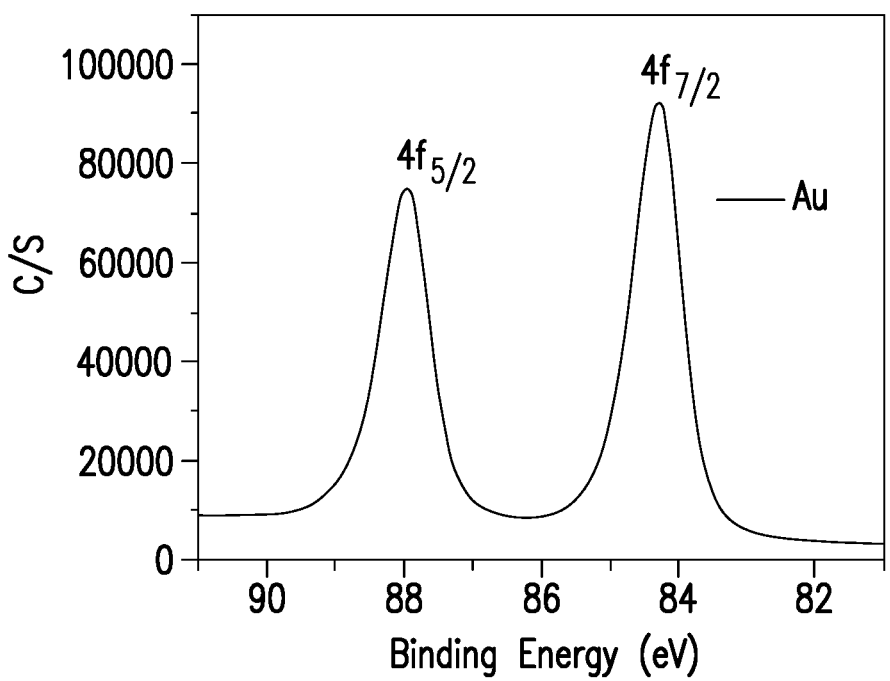
FIG. 5 shows a high resolution Au XPS spectrum of the cyanide-functionalized AuNPs.

As shown in FIG. 5, Au 4f peaks 4f$_{5/2}$ at 88 eV and 4f$_{7/2}$ 84.3 eV with a well separated spin-orbit components ($\Delta$=3.7 eV) of an asymmetric peak shape were observed. This confirms the presence of metallic Au nanoparticles. The presence of Au 4f$_{7/2}$ located at 84.3 eV, which is higher than for bulk Au (0) (83.8 eV), is attributed to functionalized Au nanoparticles at the surface of reduced Au core.

Figure 6:
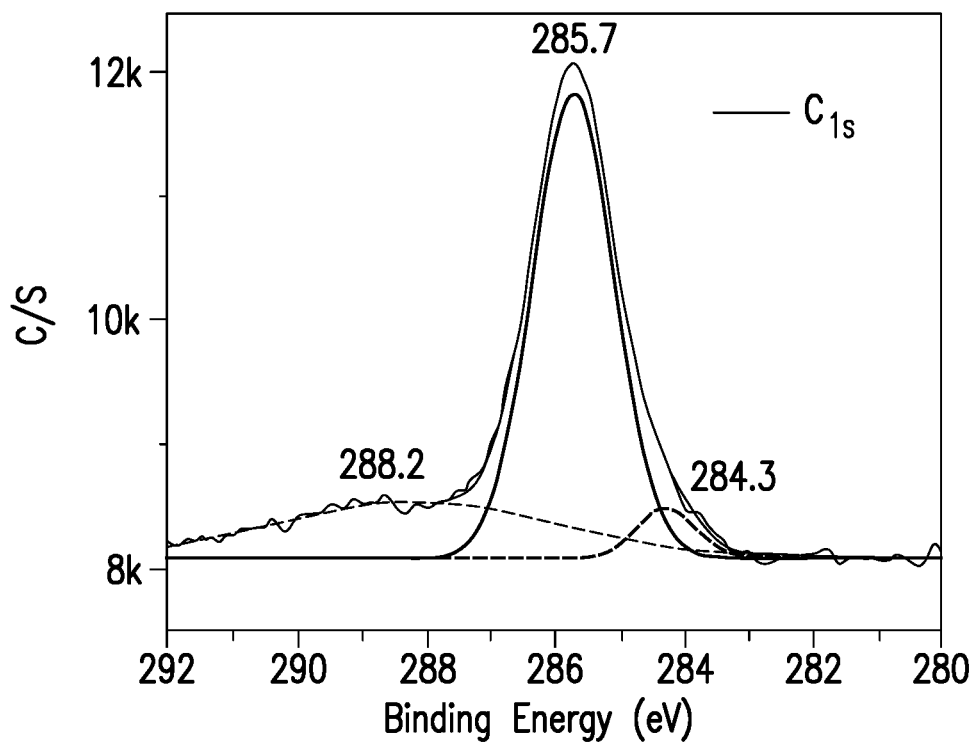
FIG. 6 shows a high resolution C1s XPS spectrum of the cyanide-functionalized AuNPs.

As shown in FIG. 6, the high resolution C1s XPS spectrum of cyano functionalized Au Nanoparticles. It shows a board peak around 286 eV. Deconvolution of the spectrum shows peaks corresponds to C—C (284.3 eV), C—N (285.7 eV) and C=N/C=O (288.2 eV).

Figure 7:
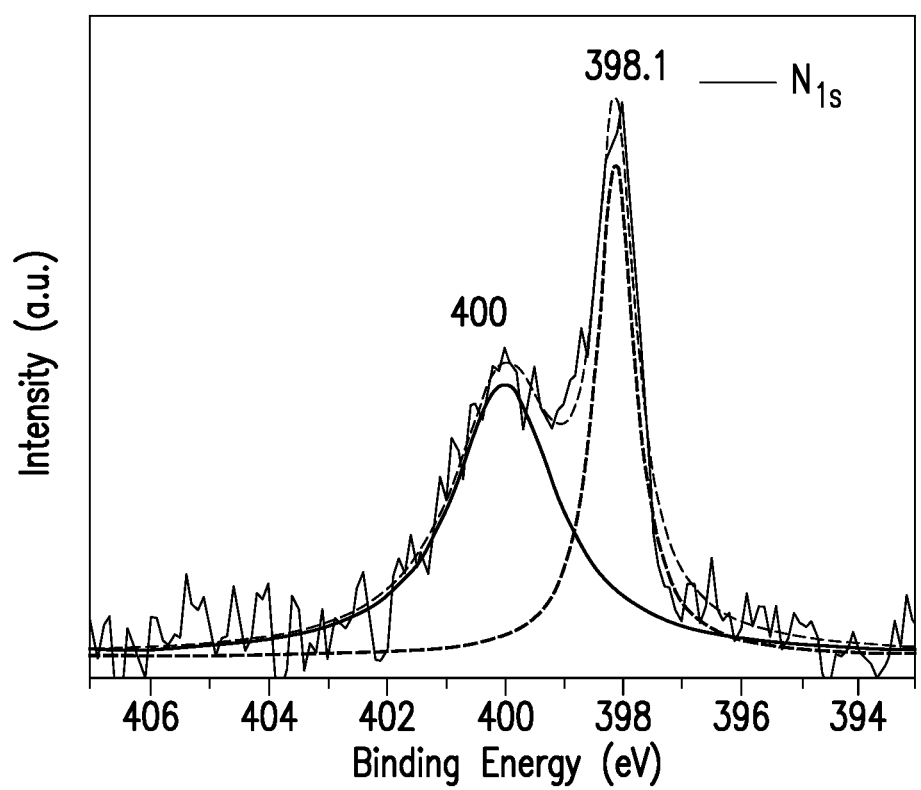
FIG. 7 shows a high resolution N1s XPS spectrum of the cyanide-functionalized AuNPs.

As shown in FIG. 7 high Resolution N1s XPS analysis of cyano functionalized Au Nanoparticles. It shows the peak around 400 eV and 398.1 eV corresponds to C=N and C—NH$_2$ respectively. Which is further confirmed by the deconvolution analysis of the spectrum.

Further elemental analysis form XPS shows the presence of N on the surface of the Au. The Table provides the XPS atomic concentration. The total concentration of N is around 5% is present.

|  | Elements | | | |
| --- | --- | --- | --- | --- |
|  | C1s | N1s | O1s | Au4f |
| RSF | 0.314 | 0.499 | 0.733 | 6.805 |
| Corrected RSF | 7.458 | 12.022 | 17.925 | 183.032 |
| Concentration | 33.85 | 5.03 | 28.29 | 32.83 |

Set forth below are some embodiments of the foregoing disclosure:

Embodiment 1: A cyanide-functionalized gold nanoparticle.

Embodiment 2: The cyanide-functionalized gold nanoparticle as in any prior embodiment, having an average diameter of about 10 to about 200 nm.

Embodiment 3: The cyanide-functionalized gold nanoparticle as in any prior embodiment, wherein the cyanide covers about 0.1% to about 40% of the nanoparticle surface.

Embodiment 4: A method of making cyanide-functionalized gold nanoparticles, the method comprising forming an aqueous reaction mixture comprising a gold precursor and glycine, keeping the reaction mixture at about 18° C. to about 50° C. for at least 6 days to provide formation of the cyanide-functionalized gold nanoparticles, and isolating the cyanide-functionalized gold nanoparticles from the reaction mixture.

Embodiment 5: The method as in any prior embodiment, wherein keeping the reaction mixture about 18° C. to about 50° C. for at least 6 days is done in the dark without stirring.

Embodiment 6: The method as in any prior embodiment, wherein the gold precursor comprises K[AuCl$_4$], chloroauric acid, gold (III) chloride; gold (III) iodide, trichloro(pyridine)gold(III), chloro(triphenylphosphine)gold(I), gold(I) cyanide, gold(III) bromide, gold(I) sulfide, gold(III) hydroxide, chloro(triethylphosphine)gold(I), methyl(triphenylphosphine)gold(I), or a salt thereof.

Embodiment 7: The method as in any prior embodiments, wherein the pH of the reaction mixture is about 7 to about 14.

Embodiment 8: The method as in any prior embodiment, wherein the reaction mixture comprises 0.001 to 1 wt % of the gold salt, and 0.001 to 1 wt % of the glycine, based on the weight of the reaction mixture.

Embodiment 9: The method as in any prior embodiments, further comprising monitoring the formation of the cyanide-functionalized gold nanoparticles by UV-visible spectroscopy, dynamic light scattering particle analysis, Raman spectroscopy, or a combination comprising at least one of the foregoing.

Embodiment 10: The method as in any prior embodiments, wherein the cyanide-functionalized gold nanoparticles have an average diameter of about 10 to about 200 nm.

Embodiment 11: The method as in any prior embodiments, wherein the cyanide covers about 0.1% to about 40% of the nanoparticle surface.

Embodiment 12: A method of analyzing a sample, comprising contacting cyanide-functionalized gold nanoparticles with the sample and performing an analytical method on the sample.

Embodiment 13: The method as in any prior embodiments, wherein the cyanide-functionalized gold nanoparticles provide an internal reference; and wherein the analytical method comprises radiating the sample contacted with the cyanide-functionalized gold nanoparticles with electromagnetic radiation; measuring a Raman spectrum emitted from the sample; and determining the presence or a concentration of a selected chemical in the sample from the Raman spectrum, wherein the cyanide-functionalized gold nanoparticles provide an internal reference at about 2,100 cm$^{-1}$.

Embodiment 14: The method as in any prior embodiments, wherein the analytical method is SERS.

Embodiment 15: The method as in any prior embodiments, wherein the cyanide-functionalized gold nanoparticles are in the form of a sol, a gel, a substrate comprising a support layer, or a matrix.

Embodiment 16: The method as in any prior embodiments, wherein the cyanide-functionalized gold nanoparticles have an average diameter of about 10 to about 200 nm.

Embodiment 17: The method as in any prior embodiments, wherein the sample is a biological sample, and the method comprises detecting a biological analyte in the biological sample.

Embodiment 18: A sensor comprising the cyanide-functionalized gold nanoparticle as in any prior embodiments.

Embodiment 19: The sensor as in any prior embodiments, wherein the sensor 200 comprises an optically sensitive material 202 comprising the cyanide-functionalized gold nanoparticles, and wherein the optically sensitive material 202 is dispersed in a matrix material 204.

Embodiment 20: The sensor as in any prior embodiments, wherein the sensor 100 comprises electrodes 10 and the cyanide-functionalized gold nanoparticles 30 bridging a gap between the electrodes 30.

The use of the terms "a" and "an" and "the" and similar referents in the context of describing the invention (especially in the context of the following claims) are to be construed to cover both the singular and the plural, unless otherwise indicated herein or clearly contradicted by context. Further, it should be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

The teachings of the present disclosure may be used in a variety of well operations. These operations may involve using one or more treatment agents to treat a formation, the fluids resident in a formation, a wellbore, and/or equipment in the wellbore, such as production tubing. The treatment agents may be in the form of liquids, gases, solids, semi-solids, and mixtures thereof. Illustrative treatment agents include, but are not limited to, fracturing fluids, acids, steam, water, brine, anti-corrosion agents, cement, permeability modifiers, drilling muds, emulsifiers, demulsifiers, tracers, flow improvers etc. Illustrative well operations include, but are not limited to, hydraulic fracturing, stimulation, tracer injection, cleaning, acidizing, steam injection, water flooding, cementing, etc.

While the invention has been described with reference to an exemplary embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited.

What is claimed is:

1. A method of making cyanide-functionalized gold nanoparticles, the method comprising:
    forming an aqueous reaction mixture comprising a gold precursor and glycine,
    keeping the reaction mixture at about 18° C. to about 50° C. for at least 6 days to provide formation of the cyanide-functionalized gold nanoparticles, and
    isolating the cyanide-functionalized gold nanoparticles from the reaction mixture.

2. The method of claim 1, wherein keeping the reaction mixture about 18° C. to about 50° C. for at least 6 days is done in the dark without stirring.

3. The method of claim 1, wherein the gold precursor comprises $K[AuCl_4]$, chloroauric acid, gold (III) chloride; gold (III) iodide, trichloro(pyridine)gold(III), chloro(triphenylphosphine)gold(I), gold(I) cyanide, gold(III) bromide, gold(I) sulfide, gold(III) hydroxide, chloro(triethylphosphine)gold(I), methyl(triphenylphosphine)gold(I), or a salt thereof.

4. The method of claim 1, wherein the reaction mixture has a pH of about 7 to about 14.

5. The method of claim 1, wherein the reaction mixture comprises 0.001 to 1 wt % of the gold precursor, and 0.001 to 1 wt % of the glycine, based on the weight of the reaction mixture.

6. The method of claim 1, further comprising monitoring the formation of the cyanide-functionalized gold nanoparticles by UV-visible spectroscopy, dynamic light scattering particle analysis, Raman spectroscopy, or a combination comprising at least one of the foregoing.

7. The method of claim 1, wherein the cyanide-functionalized gold nanoparticles have an average diameter of about 10 to about 200 nm.

8. The method of claim 1, wherein the cyanide in the cyanide-functionalized gold nanoparticles covers about 0.1% to about 40% of the nanoparticle surface.

* * * * *